United States Patent

Kosak et al.

[11] Patent Number: 5,968,729
[45] Date of Patent: Oct. 19, 1999

[54] USE OF CENTRIFUGATION TO PREPARE A RETRACTABLE SEAL OVER REAGENTS IN A REACTION CONTAINER

[76] Inventors: Kenneth M. Kosak, 3194 S. 4400 West, West Valley City, Utah 84120; Matthew K. Kosak, 272 E. New Century La., #F72, Salt Lake City, Utah 84115

[21] Appl. No.: 09/049,707

[22] Filed: Mar. 28, 1998

Related U.S. Application Data

[63] Continuation-in-part of application No. 08/918,374, Aug. 26, 1997, which is a continuation-in-part of application No. 08/257,567, Jun. 10, 1994, Pat. No. 5,550,044.

[51] Int. Cl.⁶ .............................. C12Q 1/00; C12Q 1/68; G01N 33/53; C12P 19/34
[52] U.S. Cl. .................... 435/4; 435/6; 435/7.1; 435/41; 435/89; 435/91.1; 435/91.4; 435/91.41; 435/174; 435/177; 435/182; 436/528; 436/535; 530/812; 530/817
[58] Field of Search .............................. 435/4, 6, 7.1, 41, 435/89, 91.1, 91.4, 91.41, 174, 177, 182; 436/528, 535; 530/812, 817

[56] References Cited

U.S. PATENT DOCUMENTS

| | | | |
|---|---|---|---|
| 4,384,835 | 5/1983 | Bland | 425/7 |
| 4,607,050 | 8/1986 | Kieran et al. | 514/520 |
| 4,919,841 | 4/1990 | Kamel | 252/186.26 |
| 4,927,545 | 5/1990 | Roginski | 210/745 |
| 5,106,633 | 4/1992 | Edens et al. | 426/8 |
| 5,200,236 | 4/1993 | Lang et al. | 427/213 |
| 5,364,591 | 11/1994 | Green et al. | 422/58 |
| 5,413,924 | 5/1995 | Kosak et al. | 435/177 |
| 5,550,044 | 8/1996 | Kosak et al. | 435/177 |
| 5,576,197 | 11/1996 | Arrold | 435/91.2 |
| 5,643,764 | 7/1997 | Kosak et al. | 435/91.1 |

*Primary Examiner*—David M. Naff

[57] ABSTRACT

A method is provided using centrifugation to prepare a seal of solidified wax, grease or polymer mix over an aqueous reagent in a reaction container such that the reagent is separated from contact with the atmosphere. The amount of solidified wax, grease or polymer mix is not sufficient when melted to a liquid to separate the reagent from contact with the atmosphere under gravity. A reagent and solidified wax, grease or polymer mix are combined in a container. During centrifugation and heating, the solidified wax, grease or polymer mix melts to a liquid, and centrifuging causes the liquid to form over the reagent a layer that completely separates the reagent from the atmosphere. As centrifugation continues, the liquid is cooled and solidified to form the seal. Additional reagents are preferably added on top of the seal such that when the container is heated and the seal melted the upper and lower reagents mix for reaction. Preferred use of sealing reagents by this method is in polymerase chain reaction (PCR), reverse transcriptase reactions, nucleic acid sequencing, and colorimetric, fluorometric or chemiluminescent labeled immunoassays.

20 Claims, No Drawings

USE OF CENTRIFUGATION TO PREPARE A RETRACTABLE SEAL OVER REAGENTS IN A REACTION CONTAINER

This is a continuation-in-part application of U.S. patent application Ser. No. 918,374, filed Aug. 26, 1997, which is a continuation-in-part application of Ser. No. 257,567, filed Jun. 10, 1994, now U.S. Pat. No. 5,550,044, issued Aug. 27, 1996. The disclosures in the above applications are hereby incorporated into this patent application by reference.

FIELD OF THE INVENTION

This invention is for the preparation and use of chemical reaction containers or tubes preloaded with one or more reagents that are sealed under a retractable layer of wax that is thinner than is normally possible. The small amount of wax used in this invention is insufficient to spontaneously cover the aqueous layer. This is because when the amount of wax provided herein is melted over the aqueous reagent under gravity alone, most of the wax moves to the sides of the container. This leaves a central hole in the wax layer that allows contact of the reagent solution with the atmosphere. However, in this invention, the molten wax is centrifuged, forcing the wax down over the aqueous surface to form a complete seal as it is cooled to a solid.

After the reagents are sealed under the wax layer they may be stored, or additional solutions with reagents may be added on top of the wax and remain separated from the sealed reagents. The sealed reagents are subsequently released by heating to melt the wax layer, at which time the reagents can mix. Since the original seal retracts and is destroyed when it is melted, this is a non-barrier system in that no wax barrier remains after the reaction is initiated. This invention is for use in various in vitro chemical, biochemical and immunological reactions.

DESCRIPTION OF THE PRIOR ART

The task of running chemical reactions is made more convenient and consistent through preloading the reaction containers with premeasured aqueous reagent. In the prior art, a convenient way to seal the aqueous reagent in the container is to cover it with a layer of solid wax. This provides protection of the reagent from the atmosphere and excessive evaporation, and allows for storage of the containers for future use. Such wax sealed, preloaded containers or tubes, are of particular importance in certain biochemical reactions. Some examples are nucleic acid hybridizations, the reverse transcriptase reaction (RTR), used to produce complementary DNA (cDNA) from RNA (Biochemistry 30, 7661–7666, 1991), and in DNA sequencing procedures.

Wax sealed, preloaded tubes are also useful in nucleic acid amplification such as the polymerase chain reaction (PCR). The PCR (U.S. Pat. Nos. 4,683,202 and 4,683,195) employs a heating and cooling cycle to drive the reaction. First, the reaction mixture is heated to, or above, the nucleic acid melting temperature (denaturization), then cooled to allow specific oligonucleotide primers to bind to the sample (annealing), and then heated to optimize the addition of complementary bases to the amplified nucleic acid (extension). Using heat stable, *Taq* DNA polymerase (U.S. Pat. No. 4,889,818), this cycle of denaturing, annealing and extension is repeated as many times as needed to generate the desired product.

The PCR has become a major tool in molecular biology, where there is a need for high specificity during amplification. One method for increasing specificity is pre-amplification heating. H. A. Erlich, et al, Science 252, 1643–1651 (1991), and R. T. D'Aquila, et al, Nucleic Acids Res. 19, 3749 (1991) have described this method. It requires exclusion of at least one essential reagent (dNTP's, $Mg^{2+}$, DNA polymerase or primers), from the reaction until it has been heated to the desired annealing temperature. However, the procedure generally requires the sample tubes to be closed until heated, and then reopened for addition of the missing reagent.

The procedure, also called "hot start" PCR, has been improved in the prior art by the use of a non-retractable wax barrier or seal, formed in the reaction tube that separates some of the reagents until the tube is heated to melt the barrier. Perkin Elmer Corporation, Norwalk, Conn., now sells a wax pellet (Ampliwax™) for this purpose. Their published procedure includes the steps of: (1) to a sample tube containing primers, $Mg^{2+}$, dNTP's in buffer, add one pellet of Ampliwax™; (2) heat the tube to 80° C. to melt the wax; (3) cool to room temperature to form a wax barrier on top of the solution; (4) over the wax barrier, add the sample with DNA polymerase in buffer; and (5) start normal PCR cycling.

The uses for Ampliwax™ and greases, to form non-retractable barriers between reagents in a reaction tube are more fully disclosed in U.S. Pat. No. 5,411,876, by Will Bloch, et al. The Bloch, et al patent requires a sufficient mass of wax or grease to spontaneously form a vapor barrier over an aqueous sample in a PCR reaction tube. Wax or grease is cast as a molten layer, where gravity spreads the molten layer over an aqueous solution. The molten layer is allowed to cool and solidify and is then used as a barrier between subsets of PCR reagents within the reaction tube. The method teaches that a sufficient mass of wax be used to form a vapor barrier of molten wax during the reaction as well as form a barrier after cooling the wax to a solid.

Also, U.S. Pat. No. 5,576,197 by R. Arnold, discloses a PCR container with a mass of wax attached to the inside surface. As with the Ampliwax™, this patent also requires that the mass of wax be of sufficient mass that it will spontaneously cover the aqueous solution to form a non-retractable seal even after the reaction has been stopped.

Arnold also describes the disadvantages of a centrifugation method called "phase inversion". In this method a PCR solution is added to solid wax in a tube and centrifuged to force the liquid phase through the solid wax. Apparently an excessive length of time and extremely high speeds are required to generate the necessary force. Arnold describes several problems with the centrifugation method. One problem is that some of the aqueous liquid can become trapped in the wax and react violently when heated. Also, reagents can absorb onto the solid wax, which removes them from the PCR.

Contrary to Arnold, who teaches against centrifugation, the applicants have discovered that centrifugation can work if it is used in a different method. Instead of using phase inversion, the instant invention requires that the wax must be molten before or during centrifugation. As will be shown below, the use of molten wax avoids all the problems of solid wax.

Horton, et al, Biotechniques Vol. 16, No. 1, (1994), disclose a method that employs petroleum jelly to form a spontaneous seal over a reagent in a tube that is then overlaid with oil to carry out hot start PCR. Horton, et al also teaches away from the use of a wax and oil mixture due to the "opaque slurry" that it forms. Also, the reference points out that freezing wax seals is not recommended in the 1991 Ampliwax® product insert.

Apparently, no one in the prior art tried or even contemplated centrifuging molten wax. This may be true since there is no convenient way to keep wax molten while centrifuging it. As far as the applicants can determine, all laboratory centrifuges are specifically designed to cool samples off by circulation of air or by refrigeration. As is explained below, this was a difficulty that the applicants had to overcome in order to centrifuge molten wax.

In the prior art of preparing solid wax layers or seals over aqueous solutions in a container, it is known that the molten wax, like oil, is normally spread by gravity over the aqueous surface. The molten wax forms a meniscus, so that the wax layer is noticeably thinner in the center than at the perimeter or sides of the container (see Bloch, et al, col. 26, lines 60–68). After the wax has solidified, it maintains the meniscus shape, and in a relatively narrow container such as a PCR reaction tube, the wax forms a crater-like depression. Under these conditions, an insufficient amount of wax will leave a central hole at the bottom of the solidified meniscus, leaving the aqueous solution exposed to the atmosphere.

In the prior art, in order to have a wax seal form spontaneously over an aqueous solution under gravity, it must be non-retractable. Non-retractable means there must be enough wax mass to overcome the meniscus problem and close any potential hole at the center. Consequently, under normal gravity conditions that allow a deeper wax meniscus to form, a larger mass of wax is required.

This is a serious problem because, as Bloch, et al have emphasized, it is important to keep the total mass of wax as low as possible when performing reactions such as the PCR. Bloch, et al describe several problems that result from having to use too much wax to prepare the required seals to form spontaneously over an aqueous reaction solution or sample (see col. 14, line 65 through col. 15, line 8 and also col. 8, line 55 through col. 9, line 31). First, too much wax can make it difficult to mechanically penetrate the wax seal in order to recover the aqueous sample. Second, too much wax can clog or plug the pipette tip, preventing aspiration of the aqueous sample. Third, excess wax requires more pressure to penetrate the seal, which can cause spurting of the aqueous sample during penetration and lead to aerosol contamination problems. And fourth, which pertains mostly to the PCR, the excess mass of wax must be heated and cooled along with the aqueous sample during the thermocycling. Since the larger mass requires additional time to heat and cool compared to a smaller mass, the procedure becomes more time consuming. Therefore, a major problem in the prior art of preparing wax seals over aqueous solutions has been to find conditions that reduce the depth of the solidified wax meniscus, which in turn permits the use of a smaller mass of wax.

Through their invention and subsequent claims, Bloch, et al disclose in great detail, several ways to minimize the mass of wax needed when working under normal gravity conditions. For instance, they suggest adding a suitable surfactant to the wax and possibly to the aqueous reagent. Another remedy is to employ plastic reaction tubes with a hydrophilic internal surface, prepared by complicated coating procedures with surfactants, or possibly plasma etching the container. Yet another suggestion is to add certain types of buoyant plastic mesh or particles to the wax.

The methods disclosed by Bloch, et al require either adding certain substances or materials to the wax, or modifying the physical surface of the container. Their methods require testing the various additives for purity and/or lack of interference, or complicated procedures for altering the container surface. There is no suggestion or teaching of solving the problem with centrifugation. Contrary to the teachings and suggestions of Bloch, et al, it has been discovered that additives to the wax and/or modifications to the container are not required for reducing the mass of wax.

Cummins, et al, U.S. Pat. No. 5,364,591, disclose a device for performing PCR with beads or particles that are moved from one chamber to another. The chambers are separated by barriers that must be pierced. In one method, centrifugation may be used to force the beads through the barrier layer between confined chambers. This procedure uses centrifugation of a solid phase to destroy a barrier and teaches away from the function of the instant invention, where centrifugation is used to create a seal rather than destroy one.

The use of centrifugation to separate various materials into zones based on their relative density or buoyancy is well known. For instance, E. T. Roginski, U.S. Pat. No. 4,927,545, has disclosed a method and apparatus for monitoring the separation of red blood cells from serum during centrifugation. In that method, as in other centrifugation methods, more dense materials such as red blood cells are allowed to pass through a separating fluid of specified density, while less dense materials, such as serum, are not. These procedures require passage of materials through a hydrophilic fluid to form a three phase system with an aqueous phase that remains exposed to the atmosphere. This teaches away from the function of the instant invention, which requires melting a solid to a liquid and formation of a two phase system sealed. Subsequently, the melted wax is cooled back to a solid during centrifugation to form a hydrophobic layer to seal the aqueous phase from the atmosphere.

Edens, et al, U.S. Pat. No. 5,106,633, discloses live yeast cells immobilized within a wax coating inside a container to act as an oxygen scavenger. Edens, et al, is using wax to solve very different problems, since; (1) there is no mention of centrifugation, and (2) the invention is a coating on the inside surface of a container, not in the form of a seal caste over an aqueous reagent. None of these disclosures teach or suggest preparing preloaded containers or tubes using centrifugation.

The methods and reagents disclosed in the references herein are hereby incorporated into this patent application by reference. As will become apparent with the disclosures to follow, the instant invention solves several problems in preparing wax seals for the PCR as well as in other high temperature enzymatic methods such as reverse transcriptase.

SUMMARY OF THE INVENTION

This invention describes novel methods for the preparation of reaction containers that contain premeasured, aqueous reagents sealed under a retractable wax layer that is thinner than is possible without centrifugation. Preferably, the reagents sealed in the container are used for reaction with other materials (such as a buffered aqueous sample), subsequently added to the container. The invention eliminates the problems in the prior art of having to add various surfactants or other materials to the wax, or to treat the container surface. With the distinguishing step of centrifuging molten wax instead of solid wax, the invention also eliminates the problems with the phase inversion method. For instance, there is no observed entrapment of aqueous liquid in the molten wax and there is no absorption of reagents to the liquid wax.

In the wax barrier PCR methods of the prior art, the barrier is not retractable and remains in place even after melting due to the large mass. Therefore, it is necessary to add a solution of sufficient volume and/or density (i.e. use densifying agents) over the wax barrier so that when the wax is melted, the upper solution will push through the liquefied wax and mix with the lower solution (see Bloch, et al, col. 18, lines 15–35). The instant invention when applied to the PCR is a non-barrier system in that no wax barrier remains after the PCR is initiated. Therefore, the prior art restriction is eliminated because when the seal of the instant invention is melted, the barrier is destroyed. Since the barrier moves out of the way when melted, the upper solution is immediately in contact with the lower solution to facilitate mixing.

The surprising discovery was made that centrifugation at the required speed will overcome the tendency of molten wax to retract to the sides of the container. This reduces the wax meniscus and allows the use of less wax than is possible in the prior art. By experimenting with the parameters of heat, wax mass, aqueous volume, container composition and centrifugation speed, it was discovered that the mass of wax required to seal over a given aqueous volume can be reduced to less than that which is possible under normal gravity conditions. Under the proper conditions of this invention, it is possible to use a mass of wax that is normally insufficient to make a seal over a given aqueous volume.

The problems cited in the prior art of heating and cooling excess mass and of penetrating the wax layer after the reaction, are eliminated. The invention also reduces the problems of measuring and adding one or more reagents to a reaction container.

After adding an aqueous sample to the preloaded container, the container is heated to a predetermined temperature to melt the wax layer and the previously sealed reagents are released into the surrounding medium, and become available for reaction with other substances in the medium. The most preferred applications for this invention are in various types of nucleic acid hybridizations, PCR's, RTR's, nucleic acid sequencing and product generating reactions such as colorimetric, fluorometric and chemiluminescent enzyme labeled immunoassays.

A mixture of all the other needed reagents can be prepared in a separate solution. Then, the preloaded tube with entrapped reagents and the reaction mixture may be combined and held indefinitely and no reaction will occur until the medium is heated to a predetermined temperature. Several different reaction mixtures can be prepared and combined with the preloaded tubes as needed, and eventually all reactions can be initiated simultaneously. This will avoid the problem of adjusting for product differences in time-sensitive and/or kinetic reactions such as enzymatic production of colored, fluorescent or chemiluminescent products used in immunoassays and molecular biology. Preloaded tubes of certain reagents will afford protection from degradation during storage and are more easily and/or accurately dispensed.

DETAILED DESCRIPTION OF THE PREFERRED EMBODIMENTS

For the purposes of this invention, the following definitions are used.

Seal and Sealer

A seal is defined here as a hydrophobic layer that completely covers an aqueous solution within a container to form a barrier layer that completely separates the atmosphere from contacting the solution. The preferred sealer is a solid material, such as wax, grease or polymer mix, that does not easily flow when solidified at room temperature (i.e. 25° C.). The preferred sealer can be melted to form a free flowing liquid at a preferred critical temperature that has a lower density than water. Preferred melting temperatures are above room temperature especially above 30° C., the upper limit depending on the heat tolerance of the reagents used and the type of reaction employed. The sealer material is for in vitro use and is essentially inert with the surrounding medium. The sealing material is water resistant or water insoluble and is not readily dissolved with acids or bases. Therefore, there is little or no release of the aqueous reagent sealed under the sealing material when exposed to an aqueous medium below the critical temperature. This definition is meant to exclude sealing materials such as hydrogels, presently used for many drug delivery systems.

Retractable Seal

A retractable seal is defined here as a hydrophobic layer that maintains a complete seal over an aqueous solution within a container while the sealer is solidified. However, when the retractable seal is melted, the material retracts toward the sidewalls of the container leaving a central hole that allows the atmosphere to contact the aqueous solution. A non-retractable seal is a hydrophobic layer that has enough sealer mass to form a complete seal over an aqueous solution within a container even when melted. A non-retractable seal is one that forms spontaneously when melted over an aqueous solution under gravity.

Reaction Container

Reaction containers are defined as any suitable container used for containing an in vitro reaction. The suitability of the container is determined by its suitability for containing a sealer such as wax and an aqueous reagent and for centrifuging it while heated to melt the wax.

Reaction containers include any suitable tubes, wells, cups, plates or capillaries, available in various sizes, that are suitable for chemical, biochemical and enzymatic reactions such as PCR. They can be made from any suitable glass, plastic, resin or polymer including acetals, polyallomers, polycarbonates, polyurethanes, polyvinyls, polyethylenes, polypropylenes, styrenes, nylons, acrylics, rubbers, polychlorinated or polyfluorinated polymers and tetrafluoroethylenes.

The reaction containers include various tubes or plates with wells at specific distances apart to coincide with automated equipment used in various biochemical and enzymatic assays such as ELISA's, and the PCR For example, tubes available at 9 mm center spacing and in strips of 8 or 12, so that they are compatible in spacing with the conventional 96 well microtiter plate format. Also included are plates with formats of 96 tubes or wells at 9 mm center spacing. Also suitable are plates with multiple or divided wells that provide 192 or 384, or more wells per plate.

Reagent

A reagent is defined as any suitable chemical or biochemical substance used in an in vitro reaction. Reagent suitability means that it can be dissolved or suspended in an aqueous medium, preloaded into a reaction container and sealed under a hydrophobic layer such as wax that is subsequently heated to melt and release the reagent into a reaction without excessive inactivation of the reagent. The following are examples of reagents for preloaded tubes.

a. Heat Resistant Enzymes

Heat resistant enzymes are a preferred group of reagents for sealing in reaction containers or tubes. For the purposes of this invention, a heat resistant enzyme is defined as any enzyme that retains most of its activity after one hour at 40° C. under optimal conditions. Many such enzymes can be used such as those from thermophilic organisms. For example, various RNA polymerases such as from Thermus sp., or Q beta replicase from bacteriophage, also SP6, T3, T4 and T7 RNA polymerases can be used, among others. Most preferred are various thermophilic enzymes including DNA polymerases from Thermus sp. such as from *Thermus aquaticus* ("*Taq*"), *Thermus thermophilus* ("*Tth*"), *Thermus flavus* ("*Tfl*"), and *Thermus brokianus*. Also included are enzymes from Thermoccocus sp. such as *Thermococcus litoralis* ("*Tli*" or "Vent™ New England Biolabs"); from Pyroccocus sp. such as *Pyroccocus furiosus* ("*Pfu*"), *Pyroccocus woesei* ("*Pwo*"); from Thermotoga sp. such as *Thermotoga maritima* ("*Tma*"); and from Bacillus sp. such as *Bacillus stearothermophilus* ("*Bst*"). Also included are RNA and DNA ligases such as "ampligase", from Epicentre Technologies, and any "recombinant" enzymes (i.e. r*Taq*, r*Tth*, r*Tfl*, r*Tli*, r*Pwo*, r*Bst*, r*Tma* and r*Pfu*, among others). Also, any other enzymes from thermophilic microorganisms and invertebrates, including forms produced by mutations or by recombinant DNA technology. Another preferred group of enzymes are reverse transcriptases, such as from avian myeloblastosis virus, "AMV", or from Moloney murine leukemia virus "M-MLV", especially enzymes modified by point mutations or deletions such as the "SuperScript™" reverse transcriptases from Life Technologies, Gaithersburg Md. Other enzymes that can be used are restriction endonucleases, helicases, glycosylases, kinases, proteases (i.e. thermophilic protease from Thermus sp. strain Rt41A), thioredoxins, nucleases, RNAses, DNAses, phosphatases (i.e. alkaline phosphatases "AP" and bacterial alkaline phosphatases "BAP"), peroxidases (i.e. horseradish peroxidase "HRP"), glucose oxidases, galactose oxidases and many others. Preferably these enzymes have sufficient thermally stable properties naturally (i.e. by isolation from thermophilic organisms), or by suitable chemical modification, mutation, or by genetic engineering.

Also included are various derivatives, analogs and labeled forms of enzymes, such as enzymes labeled with biotin, avidin, streptavidin, digoxigenin, sulfur, cyclodextrins, fluorophores, and radioactive nuclides such as $^3H$, $^{14}C$, $^{32}P$, $^{35}S$, and $^{125}I$, among others.

b. Enzyme Substrates

Another useful group of reagents for sealing in reaction containers is any suitable substrate. For example, in the PCR, these include any labeled or unlabeled nucleotides and nucleotide triphosphates (dNTP's), any deoxynucleoside triphosphates (NTP's), any dideoxynucleoside triphosphates (ddNTP's) and ribonucleoside triphosphates. Some examples are; 2'-deoxyadenosine 5'-triphosphate (dATP), 2'-deoxycytidine 5'-triphosphate (dCTP), 2'-deoxyguanosine 5'-triphosphate (dGTP), 2'-deoxythymidine 5'-triphosphate (dTTP), 2'-deoxyuridine 5'-triphosphate (dUTP), 2'-deoxyinosine 5'-triphosphate (dITP), 7-deaza-2'-deoxyguanosine 5'-triphosphate (I-N7-dGTP), among others. Also included are members of this group labeled with radioactive nuclides such as 3H, 14C, 32P, 35S, and 125I, among others.

Also included are various derivatives, analogs and labeled forms of NTP's, dNTP's and ddNTP's, such as biotin labeled, bio-4-dUTP, and bio-11-dUTP, also dNTP's labeled with digoxigenin (i.e. DIG-UTP, DIG-dUTP, DIG-ddUTP, Biotechniques 12, 104–113 (1992)), sulfur, cyclodextrins, fluorophores, isotopes, and amino groups such as 5-(3-aminoallyl)-2'-deoxyuridine 5'-triphosphate (AA-dUTP).

Another group of enzyme substrates preferred for sealing in reaction containers is any phosphorylated enzyme substrate that produces a colored, fluorescent or chemiluminescent product when dephosphorylated, as with AP, such as 5-bromo-4-chloro-3-indoyl phosphate (BCIP) and nitro blue tetrazolium (NBT); 4-methylumbelliferyl phosphate, and any phosphorylated dioxetanes (3-(2'-spiroadamantanane)-4-methoxy-4-(3"phosphoryloxy)phenyl-1,2-dioxetane (AMPPD)) and HMPPD, among others. Also preferred for sealing in reaction containers are any substrates for peroxidases such as o-phenylenediamine (OPD), 3,3'-diaminobenzidine tetrahydrochloride dihydrate (DAB), and 3,3',5,5'-tetramethylbenzidine (TMB), among others.

c. Metal Salts

Another group of reagents for sealing in reaction containers is various salts (i.e. chlorides or sulfates), of metals such as Mg, Mn, Fe, Co, Cu, Zn, Sn, etc.

d. Nucleic Acids

Another important group for sealing in reaction containers is nucleic acids. A nucleic acid is defined as any nucleic acid sequence from any source that is suitable for use in the instant invention. Said nucleic acid includes all types of RNA, all types of DNA, and oligonucleotides including primers used in the polymerase chain reaction (PCR) or DNA sequencing, and other genetic materials including synthetic nucleic acid polymers. Also included are DNA and/or RNA fragments, and derivatives from any tissue, cells, nuclei, chromosomes, cytoplasm, mitochondria, ribosomes, and other cellular sources. Also included are modified and derivatized nucleic acid sequences including those that are coupled to or associated with other substances such as proteins, lectins, histones, polypeptides, carbohydrates, lipids, resins, steroids and hormones.

An especially important group of nucleic acids for sealing in reaction containers includes any suitable labeled or unlabeled oligonucleotides for use as hybridization probes or primers. For instance, in the PCR, any appropriate antisense (reverse) primers and sense (forward) primers can be used including those labeled with any suitable label such as biotin, AP, digoxigenin, sulfur, cyclodextrins, fluorophores, isotopes, and proteins. Also included are members of this group labeled with radioactive nuclides such as $^3H$, $^{14}C$, $^{32}P$, $^{35}S$, and $^{125}I$, among others.

e. Antibodies

Another preferred group of reagents for sealing in reaction containers are any antibodies, antibody fractions and monoclonal antibodies, including derivatives thereof.

f. Antigens

Another preferred group of reagents for sealing in reaction containers are antigens or derivatives thereof, defined as substances capable of stimulating an immunologic reaction such as the formation of antibodies in an organism or in a biological system.

g. Avidins and Streptavidins

Also included are any avidins and streptavidins including derivatives, labeled forms, fractions and avidins produced by recombinant DNA technology.

h. Biotins

Also included are any biotins, including derivatized biotins such as amino-biotins, sulfo-biotins and photobiotins.

i. Cyclodextrins

Another preferred group of reagents for sealing in reaction containers are cyclodextrins. A cyclodextrin (CD) is an oligosaccharide composed of glucose monomers coupled together to form a conical, hollow molecule with a hydrophobic interior or cavity. Said cyclodextrins (CD's), of the instant invention can be any suitable cyclodextrin, including alpha-, beta-, and gamma-cyclodextrins, and their combinations, analogs, isomers, and derivatives. Also included are altered forms, such as crown ether-like compounds prepared by Kandra, L., et al, J. Inclus. Phenom. 2, 869–875 (1984), and higher homologues of cyclodextrins, such as those prepared by Pulley, et al, Biochem. Biophys. Res. Comm. 5, 11 (1961), and soluble dimers, trimers and polymers. Some recent reviews on cyclodextrins are: Atwood J. E. D., et al, Eds., "Inclusion Compounds", vols. 2 & 3, Academic Press, New York (1984); Bender, M. L., et al, "Cyclodextrin Chemistry", Springer-Verlag, Berlin, (1978) and Szejtli, J., "Cyclodextrins and Their Inclusion Complexes", Akademiai Kiado, Budapest, Hungary (1982).

Relative Centrifugal Force or R.C.F.

Relative centrifugal force (g) is calculated from the following formula:

$$g = 1.12 \times 10^{-5} (r)(\text{rpm})^2,$$

where r=radius in centimeters, and rpm=revolutions per minute.

Wax For Sealing Containers

Wax is defined as an essentially water insoluble, hydrophobic hydrocarbon that is solid or semisolid at room temperature, but can be melted above room temperature to form a dispersible liquid that has a lower density than water. Wax includes any naturally occurring and synthetic waxes, and wax esters that have the desired melting temperature. Waxes suitable for this invention are less dense than the aqueous reagent they are used with so that they form a layer over the aqueous reagent. Also, suitable waxes have little or no adverse reactivity with the aqueous reagent.

The most preferred waxes are many natural or synthetic long chain hydrocarbons such as white waxes, paraffins, silicon waxes, polychorinated or polyfluorinated hydrocarbons, polyether waxes and polyester waxes. Some examples of paraffins and approximate melting point (m.p.), that can be used in this invention are; hexacosane (56.4° C.), hentriacosane (59° C.), octacosane (61.4° C.), nonacosane (62.7° C.), triacontane (65.6° C.), hentriacontane (67.6° C.), dotriacontane (69.5° C.), tetratriacontane (72.5° C.), pentatriacontane (74.4° C.), hexatriacontane (75.7° C.), including others with shorter or longer carbon chains. One suitable source of paraffin waxes for use in this invention are those from Fluka Chemical Corp., St. Louis, Mo., with m.p.'s of; 44–46° C., 50–52° C., 54–56° C., 58–60° C., and 68–74° C.

Other useful waxes are various plant derived waxes, including carnauba wax, ouricuri wax, candelilla wax, raphia wax, apple, cotton and cactus waxes; waxes produced by bacteria (i.e. cetyl stearate); fungi, protozoa and algae; various invertebrate waxes including insect waxes such as beeswaxes (i.e. triacontyl palmitate, palmatyl palmitate), and Coccus sp. derived waxes (i.e. lac, cochineal and Chinese insect). Also included are suitably modified derivatives and combinations of waxes, including various waxes produced by recombinant DNA technology.

Depending on the desired properties, such as melting point, inertness, solubility, buoyancy, etc., any of the waxes described here can be combined with polymers such as polyethylenes and polypropylenes in various proportions to give the desired result. Useful waxes can also be suitably chlorinated or fluorinated.

NON-WAX SEALING MATERIALS

It has been discovered that certain non-wax materials that are suitably hydrophobic and inert in many biochemical reactions such as PCR, can be used as sealing materials in the instant invention. They include certain greases, long-chain alcohols, long-chain acids, long-chain surfactants and polymers mixed with oil, that are solids at RT that can be melted to a liquid that has a lower density than water.

Greases For Sealing Containers

Preferred greases are solid or semi-solid hydrocarbons or silicones that are soft at RT and melt at about 30–80° C. to form a liquid that has a lower density than water. Some examples of preferred greases are white petrolatum (i.e. Vaseline®), low density silicone grease.

Alcohols For Sealing Containers

Certain long-chain (fatty) alcohols with even or odd numbers of carbons, have wax-like properties of melting temperature, density and inertness, and are suitable sealers. Some examples of preferred fatty alcohols (and approximate melting point), that can be used in this invention are listed below.

| Alcohol Name | M.P. ° C. | Formula |
| --- | --- | --- |
| carnaubyl | 68–69 | |
| lauryl (dodecanol) | 48 | $C_{12}H_{26}O$ |
| myristyl (1-tetradecanol) | 38 | $C_{14}H_{30}O$ |
| palmityl (1-hexadecano1) | 63–64 | $C_{16}H_{34}O$ |
| margaryl (1-heptadecanol) | 59.3 | $C_{17}H_{36}O$ |
| stearyl (1-octadecanol) | 59–60 | $C_{18}H_{38}O$ |
| arachidyl (1-eicosanol) | | $C_{20}H_{42}O$ |
| behenyl (1-docosanol) | | $C_{22}H_{46}O$ |
| lignoceryl (1-tetracosanol) | | $C_{24}H_{50}O$ |
| ceryl (1-hexacosanol) | 80 | $C_{27}H_{54}O$ |
| melissyl (1-triacontanol) | 88 | $C_{30}H_{62}O$ |
| octadecyl | 59 | |

Acids For Sealing Containers

Some examples of saturated fatty acids (and approximate melting point), that can be used in this invention are listed below.

| Saturated Acid Name | M.P. ° C. | Formula |
| --- | --- | --- |
| capric | 31.3 | |
| lauric (dodecanioc) | 48 | $C_{12}H_{24}O_2$ |
| myristic (tetradecanioc) | 58 | $C_{14}H_{28}O_2$ |
| palmitic (hexadecanioc) | 63–64 | $C_{16}H_{32}O_2$ |
| margaric (heptadecanioc) | 61 | $C_{17}H_{34}O_2$ |
| stearic (octadecanioc) | 70.5–71.5 | $C_{18}H_{36}O_2$ |
| arachidic | 76–77 | |
| behenic (docosanoic) | 81–82 | $C_{22}H_{44}O_2$ |
| tetra-cosanic | 84.5–85.5 | |
| lignoceric | 75–80 | |
| cerotic | 78 | |
| melissic | 91 | |

Some examples of unsaturated fatty acids (and approximate melting point), that can be used in this invention are listed below.

| Unsaturated Acid Name | M.P. ° C. | Formula |
| --- | --- | --- |
| tiglic | 64–65 | |
| hypogaeic | 33–49 | |
| gaidic | 39 | |
| physetoleic | 30 | |
| elaidic | 44–45 | |
| oleic (cis-9-octadecanoic) | 58–59 | $C_{18}H_{34}O_2$ |

-continued

| Unsaturated Acid Name | M.P. ° C. | Formula |
|---|---|---|
| isooleic | 44–45 | |
| erudic | 33–34 | |
| brassidic | 65 | |
| isoerudic | 54–56 | |

Some examples of esters that can be used in this invention are listed below.

| Ester Name | Formula |
|---|---|
| behenic acid stearyl ester (stearyl behenate) | $C_{40}H_{80}O_2$ |
| stearic acid lauryl ester (lauryl stearate) | $C_{30}H_{60}O_2$ |

Non-wax Polymers For Sealing Containers

The surprising discovery was made that certain polymers can be combined with oils, long-chain alcohols and long-chain acids to form non-wax polymer mixes useful as sealing materials. Some examples of polymers are polyethylenes, polypropylenes, certain gums and rubbers. Most preferred polymers are low and medium density polyethylenes and polypropylenes (Scientific Polymer Products, Ontario N.Y.), with melting points below 120° C. Also included are synthetic rubbers such as isoprene polymers, hydrogenated rubber, butadiene polymers, chloroprene polymers and butyl polymers.

Coloring Compounds

Also, under suitable conditions, the wax and other sealing materials can have coloring added to it in the form of a colored or fluorescent dye, preferably any suitable oil or fat soluble dye can be used. Some examples are, Sudan I, Sudan III, Sudan IV, Sudan Black B, Solvent Red 27 and Solvent Blue 14.

Mercantile Kits for Preloaded Containers with Wax Seals

A mercantile kit is defined as a collection of materials such as containers, reagents, buffer solutions, instructions for use, packaging, and the like, prepared as a package for sale. Any of the preloaded containers or tubes disclosed in the instant invention can readily be incorporated into a mercantile kit.

Preloaded tubes of the instant invention are very advantageous for selling in mercantile kits. For example, reagents would be sealed under wax in tubes or plates and are covered with a plastic sheet or slipped into a suitable plastic sleeve or bag to form packages which would minimize handling.

The following applications illustrate the great diversity of uses for the instant invention. With suitable modification by one skilled in the art, this invention can be applied to any of the following applications.

APPLICATIONS

A. PCR Using DNA Polymerase Enzyme Sealed In Reaction Containers

The DNA sample to be amplified is in a final volume of 0.02–0.1 ml containing; 0.5 mM each of dATP, dCTP, dGTP, and dTTP (or any other suitable labeled or unlabeled dNTP's), 0.002 mM each of any appropriate antisense (reverse) primers and sense (forward) primers, in a buffer of 2.5 mM $MgCl_2$, 500 mM KCl, 100 mM Tris-HCl, 0.1% w/v gelatin, pH 8.3.

Also included is any heat stable DNA polymerase in a suitable container preloaded under a wax seal as described herein. In this case, approximately 1–3 units of Taq DNA polymerase in about 1–20 μl of aqueous reagent entrapped under a wax seal that melts at a specific temperature (preferred range 50–100° C.). The PCR reaction is initiated when the wax seal over the DNA polymerase enzyme is melted to release the polymerase into solution.

Amplification is performed by sequential immersion in water baths or in any suitable thermal cycling machine. A "hot start" method is initiated when the sample is heated to the critical releasing temperature of the wax seal. Samples are optionally denatured at 98° C. for 30 seconds followed by 20–40 cycles of; 94° C. for 20–60 seconds, 65° C. for 20–60 seconds, 72° C. for 60–120 seconds.

B. High Temperature RTR

The instant invention is useful in high temperature reverse trancriptase reactions such those reported by A. L. Schaffer, et al, Anal. Biochem. 190, 292–296 (1990) and T. W. Myers, et al, Biochem. 30, 7661–7666 (1991). The procedure is modified in that one or more essential enzymes, such as Taq DNA polymerase, or Tth DNA polymerase, or reverse transcriptases (preferably thermostable), are first preloaded in a reaction container and sealed under a sealing material (i.e. wax), that melts at or near the desired reaction temperature (i.e. 60–80° C.). The sample containing the RNA to be transcribed in suitable aqueous solution is added over the sealing layer in the container. Then, the reaction is initiated when the container has been heated and has reached the required temperature to melt the seal and release the reagent (s). The high temperature RTR is reported to improve product specificity and destabilize many secondary structures in the template RNA, to allow more complete transcription.

C. High Temperature Nucleic Acid Sequencing

This method is based on the procedures of F. Sanger, et al, Proc. Natl. Acad. Sci. USA 74, 5463–5467 (1977), S. Tabor, et al, Proc. Natl. Acad. Sci. USA 84, 4767–4771 (1987) and M. A. Innis, et al, Proc. Natl. Acad. Sci. USA 85, 9436–9440 (1988). This method utilizes the three basic steps of annealing, labeling and extension/termination used in previous dideoxynucleotide methods (Sanger) except that the need for reopening and transferring of reaction products is reduced. For instance, the annealing and labeling reactions can be combined by preparing the template DNA in a mixture with the needed primer(s) in a suitable aqueous buffer.

A suitable sequencing enzyme such as Taq DNA polymerase and labeling mixture of dNTP's are preloaded in a reaction container and sealed under a sealing material (i.e. wax), that melts at or near the desired reaction temperature (i.e. 50–100° C.). The sample containing the DNA to be sequenced is added over the sealing layer in the container. Then, the reaction is initiated when the container has been heated and has reached the required temperature to melt the seal, denature the DNA and release the reagent(s).

D. Coupled RTR and PCR with Two Enzymes and Antibody

This invention can be used in another method where the RTR and PCR are coupled using two enzymes and an optional antibody. The first enzyme, used for the reverse transcriptase reaction, is any suitable reverse transcriptase enzyme such as from AMV, M-MLV or a thermal stable reverse transcriptase.

The second enzyme is any suitable thermal stable DNA polymerase used to perform the PCR. The optional antibody is any suitable antibody specific for inactivating the reverse transcriptase enzyme being used, and blocking it from subsequent interference with the PCR. For instance, the antibody could be monoclonal antibody specific for binding to the active binding site of the reverse transcriptase enzyme.

The DNA polymerase is first preloaded in a reaction container and sealed under a sealing material (i.e. wax), that melts at or near the desired reaction temperature (i.e. 60–80° C.). The optional antibody can be included with the sealed reagent.

In one method, the sample containing the RNA to be transcribed with the RT enzyme in suitable buffer containing dNTP's, primers, etc., is added over the sealing layer in the container. The RT reaction is done first, to synthesize cDNA from the sample RNA, keeping the temperature below the melting point of the seal material.

Then, the PCR is initiated when the container has been heated and has reached the required temperature to melt the seal and release the sealed reagent(s). The temperature is raised enough to denature the cDNA and to melt the seal. If included, the released antibody can then inactivate the RT enzyme and when the sample is thermocycled for the PCR, the DNA polymerase will amplify the cDNA under PCR conditions.

E. Other Types of PCR

With suitable modification by one skilled in the art, PCR reagents sealed in containers by the methods of this invention can be applied to a wide variety of PCR methods. These include asymmetric PCR, inverse PCR and arbitrarily primed PCR (APPCR), among others. For example, this invention is adaptable for applications to in situ PCR, described by G. J. Nuovo, et al, Amer. J. Pathol. 139, 847–854 and 1239–1244 (1991).

The enzymes of this invention are also applicable to inverted PCR (IPCR) as described by S. Takagi, et al, in Biotechniques 13, 176–178 (1992), and especially heat-soaked PCR (HS-PCR), as described by G. Ruano, et al, in Biotechniques 13, 266–274 (1992), but suitably modified so that a bolus of enzyme would be used that had been sealed in a reaction container of this invention.

F. Specific Binding Assays Using Reagents Sealed in a Reaction Container

It was discovered that the centrifugation method of the instant invention now makes it possible to prepare very thin seals in reaction containers (i.e. wells), with relatively large diameters (i.e. 6.6 mm). Some examples are 96 well "microtiter" plates of polypropylene or polystyrene. Using the centrifugation method of the instant invention, it was found that only about 24 mg of wax was required to make a seal over a 150 $\mu$l aqueous volume in polystyrene flat bottom Removawells® (0.4 ml), from Dynatech Laboratories, Chantilly, Va. However, without centrifugation, the same aqueous volume required about twice as much wax (i.e. 48 mg) to make a seal.

This type of container is widely used for binding assays in which an oligonucleotide probe, PCR primer, avidin, streptavidin, antibody, or antigen is bound or attached to the inside surface of the reaction well and used to bind other specific substances for ultimate detection. After the reaction is completed, measurements are conveniently made by directly reading the amount of light absorbance, or fluorescence, or luminescence in the sample that is in the well.

1. Sandwich Immunoassay

In one example, the instant invention can be used in a "sandwich immunoassay" where an antibody specific for an antigen to be detected (i.e. protein, virus, etc.), is bound (i.e. by various coating methods known in immunoassays), to the inside surface of the well (preferably covalently bound). To the bottom of the well is added about 100 $\mu$l of buffered solution containing a second antibody specific for the same antigen (preferably specific for a different epitope on the antigen than the first antibody). The second antibody may also be suitably labeled such as with alkaline phosphatase (AP) or peroxidase enzyme, or with a fluorescent or radioactive label. These reagents are then sealed in the container by the method of the instant invention. For example, about 24 mg of paraffin wax (i.e. mp 44–46° C.), is added and then melted and solidified during centrifugation at about 350–500 R.C.F.

A sample to be tested for the antigen in question is then added to the sealed container in a suitable volume (i.e. 100–200 $\mu$l) of buffered solution. The specific binding reaction is initiated by briefly heating the well to melt the wax seal, which allows the sample and sealed reagent to combine. During a suitable incubation period, antigen that is present in the sample will bind to the antibody on the well surface and will also be bound by the labeled second antibody to form a sandwich.

If, for instance the second antibody is labeled with AP, the excess unbound antibody and unbound sample materials are removed by washing the well with buffer (i.e. as in a standard ELISA procedure). The presence of the AP label is detected by combining the enzyme in a suitable buffer such as AP buffer (i.e. composed of 0.1 M Tris HCl, 0.2 M NaCl, 0.01 M $MgCl_2$, pH 9.5–10), with a suitable substrate that generates a detectable product. In this case, the substrate is a mixture of 5-bromo-4-chloro-3-indoyl phosphate (BCIP) and nitro blue tetrazolium (NBT), at approximately 0.17 mg/ml BCIP and 0.33 mg/ml NBT. The sample is incubated at RT to produce a colored product that is measured by absorption. Alternatively, the substrate can be one that produces a chemiluminescent or fluorescent product when dephosphorylated.

Where the label on the antibody is any suitable peroxidase such as horseradish peroxidase, the preferred buffer is more acidic such as 0.1 M sodium citrate, pH 5.0. With peroxidase, a suitable substrate is about 0.1% o-phenylenediamine (OPD), which produces a colored product that is measured by absorption at 490 nm.

There is another application of the instant invention to this type of container. For instance, after coating specific antibodies or antigen to the inside surface of the well, it would be useful to dry the well and seal the bottom surface under a thin wax layer. For example, about 24 mg of paraffin wax (i.e. mp 44–46° C.), is added to the coated well(s) and then melted and solidified during centrifugation at about 350–500 R.C.F. This would provide a removable, protective layer to the reagents bound to the well surface.

2. Hybridization Assay

The instant invention can also be used in a hybridization assay. In this example an oligonucleotide is used that has a complementary region specific for a known sequence of DNA or RNA that is to be detected (i.e. from a virus, bacterium, etc.), so that it can hybridize with it. The oligonucleotide is bound to the inside surface of the well (preferably covalently). To the bottom of the well is added about 100 μl of buffered solution containing a second oligonucleotide that can hybridize to another region of the DNA or RNA to be detected. The second oligonucleotide may also be suitably labeled such as biotin or with a fluorescent or radioactive label. These reagents are then sealed in the container by the method of the instant invention. For example, about 24 mg of paraffin wax (i.e. mp 44–46° C.), is added and then melted and solidified during centrifugation at about 350–500 R.C.F.

A sample to be tested for the DNA or RNA in question is then added to the sealed container in a suitable volume (i.e. 100–200 μl) of buffered solution. The hybridization reaction is initiated by briefly heating the well to melt the wax seal, which allows the sample and sealed reagent to combine. During a suitable incubation period, any complementary regions on the DNA or RNA that is present in the sample will bind by hybridization to the oligonucleotide on the well surface and will similarly be bound by the labeled second oligonucleotide to form a sandwich.

The excess unbound oligonucleotide and unbound sample materials are removed by washing the well with buffer (i.e. as in a standard hybridization procedure). If the label used is fluorescent, it is detected by adding a suitable buffer to the well and measuring fluorescence emission when the label is activated by a suitable U.V. light. Other label systems are detected by the appropriate methods.

PREPARATION METHODS FOR RETRACTABLE SEALS IN REACTION CONTAINERS

The following examples show preparation methods and use of this invention. Unless otherwise stated, the materials and equipment used were from the sources given below. The centrifuge used for all examples with or without modification was a table top centrifuge (IEC Model HN-SII), from International Equipment Co., Needham Hts, Mass., using a swinging bucket rotor (IEC #215). The polymerase chain reaction (PCR), was performed in a model PTC-100 thermocycler (M. J. Research, Watertown, Mass.).

A "PCR" pipettor refers to a positive displacement pipettor (Finnpipette P.C.R., 0.5–25 μl), from Labsystems, Helsinki, Finland with a disposable polypropylene tip and plunger.

A "standard" pipettor is an air displacement pipettor (Oxford Benchmate 40–200 μl), from Sherwood Medical, St. Louis, Mo., with a disposable polypropylene tip. The polypropylene, 0.2 ml PCR tubes were from Robbins Scientific Inc., Sunnyvale, Calif., and the polycarbonate, PCR plates were from Corning Costar Corp., Cambridge, Mass.

Paraffin wax was from Fluka Chemical Co., Ronkonkoma, N.Y.; buffer salts and additives, dyes, DNA, primers and dNTP's were from Sigma Chemical Co., St. Louis, Mo.; PCR enzymes and reagents were from Promega Corp., Madison Wis., Perkin-Elmer Corp., Norwalk, Conn., or Boehringer Mannheim Corp., Indianapolis, Ind.

EXAMPLE I

Preparation of Retractable Seals in Reaction Tubes Preloaded with $MgCl_2$ and Food Color (Exper. MK164) A few grams of paraffin wax, melting point 58–60° C., (Fluka), was melted in an aluminum weighing boat. Into the bottom of each of 12, 0.2 ml PCR tubes (bobbins), was dispensed 2 μl (about 2.5 mg), of the melted paraffin wax using a "PCR" positive displacement pipettor (Labsystems) with a disposable polypropylene tip and plunger. The 2.5 mg aliquots of wax were allowed to cool and solidify.

A loading solution was prepared, composed of 60 mM $MgCl_2$ in water, with about 1% of FD&C blue #1 food color (McCormick & Co., Baltimore Md.). To each of the above tubes was added 2 μl of the loading solution, using a standard air displacement pipettor (Oxford Benchmate, Sherwood Medical, St. Louis, Mo.), with a disposable polypropylene tip.

A table top centrifuge (IEC), using a swinging bucket rotor (IEC #215), with trunnion rings and metal shields (IEC #320), was adapted for this procedure. In order to hold the 0.2 ml polypropylene PCR tubes upright in the 50 ml shields for centrifugation, a "tube assembly" holding system was devised.

To prepared the tube assembly, the PCR tubes were first stacked in groups of 6. The conical bottom of each upper tube in the stack, protruded part way into the tube below it, leaving room for the solution and wax in the bottom of each tube. Each stack of 6 PCR tubes was supported in a 1.5 ml polypropylene centrifuge tube, which was then placed in a Pyrex™ glass tube, 16×100 mm. Finally, the glass tube containing the PCR tubes was placed in a 50 ml, conical bottomed, polypropylene centrifuge tube, which would then fit properly into the shield.

The heating method consisted of preheating the empty metal shields on a hot plate to about 150° C., quickly placing them into the trunnions in the centrifuge, and then immediately placing the tube assemblies containing the loaded PCR tubes previously described, into the shields. It was determined empirically that under these conditions, the internal temperature of the tube assembly reached about 94° C. in 4 minutes to melt the wax, and remained there for at least 3 more minutes before slowly cooling.

Immediately after placing the loaded PCR tube assembly into the heated shields, the centrifuge was turned on to 2500 rpm for 10 minutes. The heated shields heated the wax in the tubes above the melting point, while the centrifugation forced the melted wax to form a thin layer over the aqueous reagent in the bottom of the tube. As centrifugation continued, the tubes cooled to room temperature and the thin wax layer solidified forming a seal over the aqueous reagent.

Testing the Wax Seal

The PCR tubes were removed from the tube assembly and inspected. A thin, very flat wax layer with little or no visible meniscus, completely covered the colored aqueous reagent in each tube. The integrity of the wax layers was tested by adding a top layer of 0.1 ml of deionized water to each tube and letting the tubes sit at room temperature. After about 3.5 hours, the top layer of water in each tube was visually inspected for color. The result was that none of the tubes showed visible color in the upper water layer indicating that the wax seal was complete.

Releasing the Sealed Reagent

The 0.1 ml of water added previously was removed and 0.05 ml of deionized water was added to each tube, over the wax seal. The tubes were heated for 2 minutes at 94° C. and cooled back to room temperature. A uniform blue color was observed in all of the tubes, indicating that the seals had retracted and mixing had occurred between the originally sealed blue reagent in the bottom and the deionized water above.

The magnesium concentration in the water was determined for each tube. Indicator solution (2×) was prepared by combining 1 part of 0.1% calmagite (Sigma Chemical Co.) in water with 5 parts of 0.5 M Tris base, pH 9.0, in water. Sample was combined 1:1 with Indicator Solution. The absorbance was read at 515–520 nm using a spectrophotometer. Sample absorbance is compared to a standard curve prepared from known Mg concentrations. One hundred percent of the tubes released Mg into the water above, with absorbances ranging from 1.894 to 2.054. The calculated mean Mg concentration released was 0.055 mM with a coefficient of variation of about 6.4%.

EXAMPLE II

A Thermocycling Centrifuge and Procedure for the Preparation of Retractable Seals in Reaction Containers A thermocycling centrifuge was devised (Exper. MK166). A table top centrifuge (IEC Model HN-SII, described previously), using a swinging bucket rotor (IEC #215), was modified for rapid heating and cooling by lining the inside walls with a $5/16$ inch layer of aluminized "bubble wrap" insulation (Reflectix, Inc., Markleville, Ind.) and replacing the metal lid with 2 inch thick insulated lid of polystyrene foam. The foam lid had about 2 inch diameter holes cut into it for forcing air in and out of the centrifuge chamber. A thermometer was placed over the exit hole to monitor the inside chamber temperature.

During the heating cycle, hot air was blown into one of the holes in the lid using an 1875 watt heat gun (Model RV406, Revlon), set on high heat and blowing. The temperature was monitored with the thermometer and regulated by turning the heater off and on. For cooling, the heater element was switched off and the blower left on to blow room temperature air.

Two polypropylene "swinging" holders for centrifuging 0.2 ml PCR reaction tubes were prepared from disposable tip racks. The holders had $3/16$ inch diameter holes that held the conical bottomed PCR tubes upright. The holders were mounted on opposite positions on the rotor using two loops of stainless steel wire as bales. The bales were threaded through the rack and over the rotor hooks normally used for the trunnions, so that the holders would swing out horizontally when being centrifuged. The horizontal position is preferred so that the centrifugal force applied to the tubes is nearly parallel with the sides of the container. The centrifugal force thereby forces the reagent to the bottom of the container with the lighter, melted wax on top. The centrifugal force tends to flatten the liquid wax over the aqueous reagent, leaving the exposed surface at about a 60–90 degree angle to the walls.

For the procedure, a sufficient amount of wax was melted in a suitable container, such as a 2–6 inch diameter aluminum or glass pan. The desired mass of melted wax (i.e. 1.0 or more mg), was dispensed into the bottom of a suitable container for making wax seals, such as a 0.2–1.0 ml centrifuge tube, PCR tube or 96 well plastic plate. The aliquots of dispensed wax were allowed to cool and solidify.

An aqueous loading solution was prepared containing the desired reagents to be sealed under the wax. Each of the above containers that received a mass of wax, was loaded with a suitable volume of the loading solution by dispensing an aliquot of the loading solution into the bottom of each container using a standard pipettor.

The loaded containers were divided evenly and placed in opposing holders in the centrifuge apparatus and closed with the polystyrene insulated lid. The containers were centrifuged at about 500–2000 revolutions per minute (rpm), for 1–5 minutes, then the chamber was heated with hot air blown into the chamber while continuing to centrifuge.

Based on the combined radius of the rotor and holders, the calculated relative centrifugal force (R.C.F.), was about 34 R.C.F.'s at 500 rpm and about 302 R.C.F.'s at 1500 rpm.

The chamber temperature was maintained 10–50° C. above the melting point of the wax, for a sufficient time (i.e. about 2–5 minutes), to allow the wax to melt and form a flattened layer over the aqueous loading solution. Then, while still centrifuging, the chamber was cooled to room temperature to solidify the wax, by blowing in room temperature air with the heater off.

EXAMPLE III

Comparison of the Instant Invention with the Prior Art Method (Exper. MK173) The purpose of this example is to show that the instant invention makes it possible to seal aqueous reagent under a minimal layer of wax that is not possible with the same amount of wax using methods in the prior art. Without centrifugation, liquid wax has a tendency to retract and collect more at the inside walls so that there is much less wax in the center than at the edges of the aqueous surface. In addition, as the liquid wax cools and solidifies, it tends to contract further. The end result is that during solidification in the prior art, the wax seems to pull away from the center and leave a hole in the center of the solidified wax layer.

A total of 12 PCR tubes were prepared in duplicates of various ratios of wax to aqueous reagent. The wax used was paraffin, m.p. 58–60° C. (Fluka). The aqueous reagent consisted of 4 ml of 50% glycerol in water and 0.1 ml of 10% bromocresol green in water. The wax was melted in an aluminum weighing dish at 95° C., dispensed with a PCR pipettor into the bottoms of the tubes and allowed to cool to a solid. The aqueous reagent was dispensed using a standard pipettor.

The Method of the Instant Invention

Tubes numbered 1A, 2A, 3A, 4A, 5A and 6A were centrifuged at about 1500 rpm at RT for about 2 minutes. Then, while still centrifuging, the chamber was heated with hot air and maintained from 65–75.6° C. for about 2 minutes, then cooled down to rt in about 3 more minutes. Inspection of the tubes showed that all 6 had a flattened wax seal over the aqueous reagent.

The Method of the Prior Art

Tubes numbered 1B, 2B, 3B, 4B, 5B and 6B were placed upright in the previously described thermocycler and heated for 5 minutes at 80° C. to melt the wax, then cooled to RT. Inspection of the tubes showed the wax in tubes 1–5B had solidified over the aqueous reagent in a ring that covered the outermost edges of the solution and some of the tube wall, but left an opening or hole in the center where aqueous reagent was exposed to the atmosphere. Tube 6B had little or no wax over the aqueous reagent since the wax failed to rise to the top when melted. Apparently, the affinity between the wax and the polypropylene tube was enough to keep this small mass of wax below the surface.

Testing for a Wax Seal

To each of the prepared tubes 1A–6A and 1B–5B was added an upper layer of 0.1 ml of deionized water. In tubes numbered 1B, 2B, 3B, 4B and 5B, the bromocresol green dye immediately began mixing into the upper layer of water, showing that none of those tubes had a seal.

In contrast, the dye in tubes 1A, 2A, 3A, 4A, 5A and 6A remained below the wax layer, with no visible mixing with the upper water layer. Tubes 1A–6A were inspected the next day, and again after 3 days and there was still no mixing, showing that they were completely sealed.

Summary of Results

The following table shows the results with various ratios of wax to aqueous reagent in duplicate tubes and compares the centrifugation method of the instant invention versus no centrifugation used in the prior art gravity method.

| Centrifuged rpm | Approximate R.C.F. | 6 Polypropylene Containers | 6 Polycarbonate Containers |
|---|---|---|---|
| 1750 | 412 | sealed, no holes | sealed, no holes |
| 500 | 34 | sealed, no holes | sealed, no holes |

| Tube # | 1A | 1B | 2A | 2B | 3A | 3B | 4A | 4B | 5A | 5B | 6A | 6B |
|---|---|---|---|---|---|---|---|---|---|---|---|---|
| Mg of Wax | 2 | | 2 | | 4 | | 4 | | 4 | | 6 | |
| Ml of Reagent | .004 | | .006 | | .010 | | .020 | | .050 | | .050 | |
| Centrifuged | Yes | No | Yes | No | Yes | No | Yes | No | Yes | No | Yes | No |
| Seal Formed | Yes | No | Yes | No | Yes | No | Yes | No | Yes | No | Yes | No |

EXAMPLE IV

Comparison of Centrifigal Force Needed in Polypropylene vs. Polycarbonate Containers (Exper. MK212) The purpose was to determine how much relative centrifugal force (R.C.F.), is needed to provide a retractable wax seal in polypropylene vs. polycarbonate containers using the method of the instant invention.

The polypropylene containers were 0.2 ml PCR tube strips described previously. The polycarbonate containers were sections of the 0.2 ml wells cut from a PCR "thermowell plate" (#6510 from Corning Costar). Paraffin wax (m.p. 58–60° C.), was melted in an aluminum weighing dish at 95° C., dispensed with a PCR pipettor into the bottoms of the containers and allowed to cool to a solid.

The aqueous reagent consisted of 50% glycerol, 245 mM $MgCl_2$, and about 1.25% blue food color in water. Into the bottom of each container, 2 $\mu$l of the aqueous reagent was dispensed.

In a series of experiments, the containers were divided into groups of 6 polypropylene and 6 of polycarbonate containers. Each group was centrifuged at either 1750 rpm, 500 rpm or 250 rpm, while heated for about 2–3 minutes to about 70–82° C., then quickly cooled to about 37° C. before removing from the centrifuge.

In the containers centrifuged at 1750 rpm, the aqueous reagent was sealed under a good coating of wax that had no visible meniscus or differences in wax thickness between the sides and the centers. However, there was a visible meniscus in the wax layer in all of the other groups, indicated by more wax against the inside walls than in the center. There may also have been some evaporation from the aqueous phase in the groups centrifuged at lower rpm's.

In the containers centrifuged at 500 rpm, the aqueous reagent was sealed under a complete wax layer or coating even though it was thinner in the center. The containers centrifuged at 250 rpm had very poor seals (very thin), or no seals, with holes in the wax layer at the center of the meniscus. The presence of a hole in the wax was verified by gently probing the wax layers with a suitable length of 30 gauge Teflon tubing, to see if it could pass into the aqueous solution below the wax. The results are presented in the following table.

| Centrifuged rpm | Approximate R.C.F. | 6 Polypropylene Containers | 6 Polycarbonate Containers |
|---|---|---|---|

-continued

| Centrifuged rpm | Approximate R.C.F. | 6 Polypropylene Containers | 6 Polycarbonate Containers |
|---|---|---|---|
| 250 | 8.4 | no seal, with holes | very poor seal |

These results show that there is a minimum requirement of centrifugal force to obtain a retractable wax seal. For the ratio of wax to aqueous reagent tested, the minimum R.C.F. is between about 8.4 and 34.

To compare results with the prior art method of not centrifuging, the identical groups of 6 polypropylene and 6 polycarbonate containers that had been sealed when centrifuged at 1750 rpm were again melted upright in a thermocycler at 70° C. for 30 seconds without centrifugation, and cooled to RT. These groups were then designated as "0 rpm", and compared to the 500 rpm groups, prepared above, in a leakage test.

The leakage test is designed to detect any holes in the wax layer not detectable by the naked eye or with probing. It consisted of adding 0.02 ml of water to each container to make an over lay on the wax, and allowing them to soak at RT. Then, the containers were inspected at various soaking times to see if any of the blue colored reagent below the wax had leaked through the wax into the upper water layer. The results are shown in the table below.

| Centrifuged rpm | Approx. R.C.F. | Minutes Soaked | 6 Polypropylene Containers | 6 Polycarbonate Containers |
|---|---|---|---|---|
| 500 | 34 | 10 minutes | 0 leaked | 0 leaked |
| 0 | 1 | 10 minutes | 0 leaked | 4 leaked |
| 500 | 34 | 40 minutes | 0 leaked | 0 leaked |
| 0 | 1 | 40 minutes | 6 leaked | 6 leaked |
| 500 | 34 | 16 hours | 0 leaked | 0 leaked |
| 0 | 1 | 16 hours | 6 leaked | 6 leaked |

In the 0 rpm groups, the wax in 4 polycarbonate containers leaked within 10 minutes, and all of the 0 rpm containers showed leakage by 40 minutes. In contrast, none of the 500 rpm groups leaked at 10 or 40 minutes or even after 16 hour of soaking. These results demonstrate that the instant invention method is capable of producing a retractable wax seal in polypropylene or polycarbonate containers under conditions where a seal is not possible with the prior art method of not centrifuging.

EXAMPLE V

Comparison of Light Absorbance Through Retractable Wax Seals Prepared in Polypropylene vs. Polycarbonate Containers (Exper. MK212) The purpose was to provide an objective measurement of the comparative flatness of the meniscus in wax layers or seals that results from variations in relative centrifugal force (R.C.F.). Also, a comparison is made between polypropylene and polycarbonate containers using the method of the instant invention.

In the preparation of wax seals, the prior art has solved the problem of mining the mass of wax needed by adding surfactants that cause the melted wax to spread out more and thereby flatten the wax meniscus. In the instant invention, it was observed that flattening the meniscus of a given mass of wax using centrifugation also increases the relative thickness of the wax seal at the center. The relative thickness of wax at the center can be measured as an increase in the absorbance of light passed through the center area.

The polypropylene containers were 0.2 ml PCR tube strips and the polycarbonate containers were sections of the 0.2 ml wells cut from a PCR "thermowell plate" (#6510 from Corning Costar), as described and/or prepared in the previous example. Paraffin wax (m.p. 58–60° C.), was melted in an aluminum weighing dish at 95° C., dispensed with a PCR pipettor into the bottoms of the containers and allowed to cool to a solid. The aqueous reagent consisted of 50% glycerol, 245 mM $MgCl_2$, and about 1.25% blue food color in water. Into the bottom of each container, 2 µl of the aqueous reagent was dispensed. The containers were divided into groups of 6 polypropylene and 6 of polycarbonate containers. Each group was centrifuged at 500–1750 rpm's as listed in the table below, while heated for about 2–3 minutes to about 64–82° C., then quickly cooled to about 37° C. before removing from the centrifuge.

The result was that all centrifuged groups from 500–1750 rpm formed a retractable wax seal over the aqueous reagent. As was observed previously, the 1750 rpm groups had no visible meniscus while those prepared at lower rpm (i.e. 500 rpm), did.

For reading absorbance through the central area of the wax layers, the containers were positioned upright in polystyrene RemovaWell® strips (#11-010-6301, Dynatech Laboratories, Inc., Chantilly, Va.). The absorbance was measured from a light beam directed vertically through the middle of each tube. The spectrophotometer used was a Microwell Strip Reader, model EL301 (Bio-Tek Instruments Inc., Winooski, Vt.), with a 515 nm filter.

For a baseline, the 1750 rpm groups (from Example IV), were read for absorbance and then remelted upright in a thermocycler at 70° C. for 30 seconds without centrifugation, and cooled to RT. This procedure produced holes in the wax of these containers, which were then read again, and the absorbance values used for the "0 rpm" groups. All absorbance readings were taken before subsequent probing or leakage tests. The readings of 6 tubes in each group were averaged and presented in the table below.

| Centrifuged rpm | Approx. R.C.F. | Mean Absorbance Polypropylene | Mean Absorbance Polycarbonate |
|---|---|---|---|
| 0 | 1 | 0.921 | 0.727 |
| 500 | 34 | 0.952 | 0.863 |
| 750 | 76 | 0.985 | 0.878 |
| 1000 | 134 | 1.020 | 0.953 |
| 1500 | 302 | 1.090 | 1.010 |
| 1750 | 412 | 1.100 | 0.986 |

The results demonstrate an increase in absorbance through the center of the wax seal with increasing centrifugal force. The absorbance was highest at about 1000 rpm for polypropylene and about 1500 rpm for polycarbonate. These absorbance levels also correlate with the observation that the higher rpm groups had flatter wax layers.

EXAMPLE VI

Comparing The Mass of Wax Vs Grease Required For a Retractable Seal

The following tables show the minimum mass of wax vs petrolatum grease required to form a retractable seal over a given volume of aqueous reagent in various plastic containers, comparing the invention vs the prior art. The wax used was paraffin (m.p. 58–60° C.), from Fluka, and the petrolatum (m.p. 56–58° C.), was white petrolatum, USP (Vaseline®), from Chesebrough-Ponds Co., Greenwich, Conn. The aqueous reagents used consisted of water that usually contained about 1% food color and, in some cases, 50% glycerol, and salts. The seals were determined as complete by the lack of any observed movement or diffusion of color through the seal between the reagent and water, after soaking several hours.

The containers used were; polystyrene flat bottom Removawells® (0.4 ml), from Dynatech Laboratories, Chantilly, Va.; polypropylene conical (V-bottom) strip tubes (0.2 ml), from Robbins Scientific Corp., Sunnyvale, Calif.; polypropylene conical microfuge tubes (0.5 ml), from Fisher Scientific, Pittsburgh, Pa.; and polycarbonate plate wells (V-bottom, 0.2 ml), from Stratagene, La Jolla, Calif. Seals were prepared in the containers comparing the centrifugation method of the invention vs the gravity method of the prior art. For the centrifuge method, sealer was melted over the aqueous reagent, and centrifuged at about 340 g (R.C.F.) while it is cooled to a solid layer. For the prior art method, sealer was melted and solidified over the aqueous reagent at 1 g (no centrifuging).

The data are summarized from several experiments and are mean values from groups of 2, 4 or 6 containers.

TABLE VIa

Retractable Wax Seals

| Container | Preparation Method | Seal Diameter in mm. | Seal Mass in mg | Volume Covered in μl | Seal Mass per Surface Area in mg/mm$^2$ | Exper. # |
|---|---|---|---|---|---|---|
| Polystyrene 0.4 ml flat well | centrifuged @ 340 g | 6.6 | 24 | 150 | 0.70 | mk216 |
| Polypropylene 0.2 ml PCR strip tube | centrifuged @ 340 g | 4.1 | 2 | 50 | 0.15 | mk224 |
| Polypropylene 0.5 ml microtube | centrifuged @ 340 g | 4.3 | 2 | 50 | 0.14 | mk218 |
| Polycarbonate 0.2 ml PCR plate tube | centrifuged @ 340 g | 4.1 | 2 | 50 | 0.15 | mk224 |

TABLE VIb

Non-Retractable Wax Seals

| Container | Preparation Method | Seal Diameter in mm. | Seal Mass in mg | Volume Covered in μl | Seal Mass per Surface Area in mg/mm$^2$ | Exper. # |
|---|---|---|---|---|---|---|
| Polystyrene 0.4 ml flat well | gravity | 6.6 | 48 | 150 | 1.40 | mk216 |
| Polypropylene 0.2 ml PCR strip tube | gravity | 2.8 | 9 | 10 | 1.46 | mk218 |
| Polypropylene 0.5 ml microtube | gravity | 4.3 | 22 | 50 | 1.52 | mk224 |
| Polycarbonate 0.2 ml PCR plate tube | gravity | 4.1 | 20 | 50 | 1.52 | mk224 |

The preceding tables (VIa and VIb), show that several times more wax is required for nonretractable seals compared to retractable seals in the same containers over comparable aqueous volumes.

TABLE VIc

Retractable Grease Seals

| Container | Preparation Method | Seal Diameter in mm. | Seal Mass in mg | Volume Covered in μl | Seal Mass per Surface Area in mg/mm$^2$ | Exper. # |
|---|---|---|---|---|---|---|
| Polypropylene 0.2 ml PCR strip tube | centrifuged @ 340 g | 4.1 | 0.5 | 50 | 0.04 | mk224 |
| Polypropylene 0.5 ml microtube | centrifuged @ 340 g | 4.3 | 1 | 50 | 0.07 | mk224 |
| Polycarbonate 0.2 ml PCR plate tube | centrifuged @ 340 g | 4.1 | 1 | 50 | 0.08 | mk224 |

TABLE VId

Non-Retractable Grease Seals

| Container | Preparation Method | Seal Diameter in mm. | Seal Mass in mg | Volume Covered in µl | Seal Mass per Surface Area in mg/mm$^2$ | Exper. # |
|---|---|---|---|---|---|---|
| Polypropylene 0.2 ml PCR strip tube | gravity | 4.1 | 16 | 50 | 1.21. | mk224 |
| Polypropylene 0.5 ml microtube | gravity | 4.3 | 20 | 50 | 1.38 | mk224 |
| Polycarbonate 0.2 ml PCR plate tube | gravity | 4.1 | 14 | 50 | 1.06 | mk224 |

The preceding tables (VIc and VId), show that several times more grease is required for nonretractable seals compared to retractable seals in the same containers over comparable aqueous volumes. Also, in tables VIa and VIc, comparing retractable wax seals to retractable grease seals, less mass of grease is required in the same containers.

EXAMPLE VII

Retractable Wax Seals in PCR Reaction Tubes Preloaded with *Taq* DNA Polymerase and/or dNTP's (Exper. MK211) Paraffin wax, melting point 58–60° C., (Fluka, Milwaukee, Wis.), was melted at about 100–105° C. in an aluminum weighing boat. The containers were 0.2 ml PCR tubes connected in a strip of 12 tubes per strip (Robbins Scientific Inc., Sunnyvale, Calif.). The tubes were divided into three groups of 36 tubes, labeled A, B and C. Into each tube was dispensed about 2.1 mg of the melted paraffin wax using a PCR pipettor.

An aqueous loading solution containing PCR reagent was prepared for each group. Each solution contained either *Taq* DNA polymerase (*Taq*), at about 200 units/ml, and/or dATP, dCTP, dGTP and dTTP (collectively dNTP's), at about 1.5 mM of each. The *Taq* reagent (Promega Corp., Madison Wis.), and/or dNTP's reagent (Amresco Inc., Solon, Ohio), for each group was prepared in a dilution buffer composed of 100 mM KCl, 20 mM Tris-HCl (pH 9.0 at 25° C.), 0.2% Triton® X-100, 2.0 mM dithiothreitol and 50% glycerol in water.

The concentrations of the reagents in each loading solution were adjusted so that when 2 µl of loaded solution is released into a final volume of about 15 µl, the concentrations will be suitable for a polymerase chain reaction. A total of 2 microliters of concentrated aqueous reagent in loading solution was dispensed (loaded) into each group of tubes according to the table that follows.

| Tube Group | Sealed Reagent in 2 µl | Final Conc. After Release in 15 µl |
|---|---|---|
| A | Taq/dNTP's | 0.4 units/0.2 mM |
| B | Taq | 0.4 units |
| C | dNTP's | 0.2 mM |

The loading solution can include any suitable carrier substances or additives such as a carbohydrate, for instance glucose, sucrose, trehalose, cyclodextrins or Ficoll® (Pharmacia Inc.), or any suitable gel (i.e. agarose), protein (i.e. albumin, gelatin) or polymer (i.e. polyethylene glycol).

The strips of tubes were divided evenly and placed in opposing holders in the centrifuge and the centrifuge was closed. While centrifuging the tubes at about 1500 rpm (about 300 R.C.F.), they were held at RT for about 5 minutes, then hot air was blown into the chamber while still spinning.

Turning the heat off and on regulated the temperature so that the chamber temperature stayed above the m.p. of the wax (at about 66–77° C.), for about 3 minutes. Then, while still centrifuging, the chamber was cooled to about 37° C. to solidify the wax. Cooling was done by blowing in room temperature air with the heater off. The tubes were removed and stored for 4 days at 4° C.

The wax seals that were formed over the PCR reagents in the tubes were then tested using PCR for release of the reagent when melted. Previous tests have shown that because of the insufficient mass of wax, the centrifuged wax seal is a non-barrier system, which retracts and leaves the aqueous reagent exposed to the atmosphere as soon as it is melted. Since the PCR machine used did not have a heated lid to prevent condensation inside the tubes, a 28 mg paraffin wax bead (Lot #1119, Lumitekk, SLC Utah), was added to each tube to provide a vapor barrier during the PCR The preloaded PCR reagents were tested in the PCR using commercially available "PCR buffer" (Promega), containing DNA template and PCR primers. The PCR buffer was composed of 50 mM KCl, 10 mM Tris-HCl (pH 9.0 at 25° C.), 0.1% Triton® X-100, in water. The DNA template to be amplified was pBR322 plasmid DNA from E. coli (Sigma Chemical Corp). The 16 base oligonucleotide primers were pBR322 EcoR I (clockwise) and pBR322 BamH I (counter-clockwise), (both Promega), which complement the ends of a 393 base pair segment on the pBR322 DNA.

A PCR "master mix" was prepared in PCR buffer without any dNTP's, or *Taq*. The master mix contained 2.5 mM MgCl$_2$, about 0.002 micrograms of pBR322 DNA, and about 0.04 nanomoles of each primer in PCR buffer, for each reaction volume of 0.015 ml. After dispensing 0.015 ml of master mix into each of three sealed tubes from each group, either buffer only, 0.4 units of *Taq* or dNTP's (about 0.2 mM final), were added in buffer as needed. Tubes of group A received buffer only, group B received dNTP's, and group C received *Taq*.

For the PCR, the samples were thermocycled for 35 cycles of; 60 seconds @ 94° C., 30 seconds @ 55° C., and 60 seconds @ 72° C. The PCR products were analyzed by a standard method of agarose gel electrophoresis (AGE).

The triplicate samples A, B and C were diluted about ⅔ in gel loading solution (Sigma Cat# G2526). About 8 µl of each diluted sample was loaded into corresponding wells in a 3% agarose gel in TBE buffer (89 mM Tris, 89 mM borate, 2 mM EDTA, pH 8), containing 0.5 micrograms/ml of ethidium bromide stain. The AGE was run horizontally for about 1 hour at 100 volts and 50 milliamps, then subilluminated with U.V. light and photographed with Polaroid® #665 instant film.

With U.V. illumination, PCR product was visible as fluorescent bands in the gel for all three groups. These results indicate that the paraffin sealed PCR reagents were released from under the seal during the PCR and were active enough after 4 days storage at 4° C. to produce amplified pBR322 DNA.

EXAMPLE VIII

Properties of Various Non-Wax Polymer Mixes for Sealing Reaction Containers (Exper. KK188, 209, 211) The following is a list of polymers tested for their physical properties and for use as sealing materials in reaction containers.

Atactic polypropylene (APP), stiff, sticky, translucent grease-like paste, softening point 20° C., density 0.8544, Cat #783, Scientific Polymer Products (SPP), Ontario, N.Y.

Low density polyethylene (LDPE), stiff translucent grease-like paste, mp 92–117° C., SPP Cat #535.

Medium density polyethylene (MDPE), white opaque powder, mp 109–111° C., Cat #33,211-9, Aldrich Chemical Co.

Stearyl alcohol (1-octadecanol), white opaque powdery flakes, mp 59° C., Sigma Chemical Co.

Various polymer mixes were prepared, combining certain polymers with long chained alcohol or with heavy mineral oil (U.S.P. grade), or combinations of polymer, alcohol and oil. The mixtures were prepared by melting them over a hotplate in 20 ml glass scintillation vials and stirring with a stainless steel wire or a glass rod until homogeneous. The ratios are by weight. The melting points were estimated by placing a few milligrams of each material on the inside of a polypropylene reaction tube in a thermocycling machine. As the machine was heating, the temperature range was noted when the mixture began flowing and appeared liquefied.

Various mixtures of the non-wax polymers were tested for their ability to form non-retractable (spontaneously with gravity) seals and/or retractable seals over an aqueous solution. The tests for seals with gravity were performed by adding about 25 µl of molten material to 50 or 100 µl of blue colored water in a 0.2 ml polypropylene PCR tube. After melting at about 95° C. and cooling to solidify, the presence of a complete seal was determined by the lack of a visible hole in the layer of mix material. All of the mixtures described are capable of forming suitable seals over an aqueous reagent. Most preferred are mixtures B through P.

Mixture A is a 1:1 ratio of APP+Oil. This formed a clear liquid with a slight yellow cast when melted and a very thick, foggy syrupy gel when cooled to room temperature (RT).

Mixture B is a 1:1 ratio of LDPE+Oil. This formed a clear colorless liquid when melted and a moderately stiff foggy solid mass when at RT, mp about 70–72° C. Two out of three tubes formed good barriers.

Mixture BB is a 2:1 ratio of LDPE+Oil. This formed a stiff foggy solid mass when at RT, mp about 80° C. All three tubes formed a barrier with 25 mg over 50 µl of water.

Mixture C is a 1:1 ratio of MDPE+Oil. At RT this formed a soft, opaque waxy solid mass, mp greater than 95° C.

Mixture D is a 1:1 ratio of APP+Oil. At RT this formed a stiff, pale yellow opaque solid mass.

Mixture E is a 2:1 ratio of APP+Oil. At RT this formed a flowable, pale yellow solid mass.

Mixture F is a 1:2 ratio of LDPE+Oil. At RT this formed a soft, foggy white solid mass, mp about 70–75° C. All three tubes formed barriers with about 25 µl material over 100 µl water.

Mixture G is a 1:6:1 ratio of LDPE+1-Octadecanol+Oil. At RT this formed a hard, waxy white opaque solid, mp greater than 60° C.

Mixture H is a 1:9:2 ratio of LDPE+1-Octadecanol+Oil. At RT this formed a hard, waxy white opaque solid, mp greater than 60° C.

Mixture I is a 1:3 ratio of LDPE+1-Octadecanol. At RT this formed a hard, waxy white opaque solid, mp greater than 60° C.

Mixture J is a 1:1 ratio of 1-Octadecanol+Oil. At RT this formed a semi-hard, oily white opaque solid, mp about 58° C.

Mixture K is a 1:2:1 ratio of APP+1-Octadecanol+Oil. At RT this formed a soft, oily and flaky material, mp 60–65° C.

Mixture L is a 1:3:2 ratio of LDPE+1-Octadecanol+Oil. At RT this formed a slightly brittle, slightly oily white opaque solid, mp about 60° C.

Mixture M is a 1:4:1 ratio of LDPE+1-Octadecanol+Oil. At RT this formed a brittle, white opaque solid, mp about 63–70° C.

Mixture N is a 1:1:1 ratio of LDPE+1-Octadecanol+Oil. At RT this formed a stiff, sticky, white opaque, grease-like solid mass, mp about 70–75° C.

Mixture O is a 1:2:2 ratio of LDPE+1-Octadecanol+Oil. At RT this formed a slightly brittle, slightly oily white opaque solid.

Mixture P is a 1:3 ratio of LDPE+Oil. At RT this formed a soft, foggy, grease-like solid mass, mp about 60–70° C. This material works well in forming spontaneous seals and in forming retractable seals when centrifuged at 60–70° C. over an aqueous reagent and cooled to RT during centrifugation.

The retractable sealing characteristics were compared between mixture P, paraffin wax (mp 58–60° C.) and petroleum jelly (Vaseline®). About 2.5 mg of each material was melted and added to 0.2 ml PCR tubes (24 per group). Then 5 µl of blue colored 1× PCR buffer was added to each tube. Retractable seals were formed over the aqueous reagent by centrifuging at about 1500 rpm (about 300 R.C.F.), and heating the tubes to about 76° C. for about 1 minute. While still centrifuging, the tubes were cooled to RT to solidify the layers.

All of the materials formed thin, flat, retractable seals over the aqueous reagent. The tubes were weighed and then subjected to 5 cycles of freezing at −85° C. and thawing at RT (25° C.). Inspection of the seals showed that the seals using the non-wax mixture P were unaffected. However, the wax seals appeared slightly tilted and the Vaseline® seals were slightly more tilted, indicating that some dislodging of those seals occurred during the freezing and thawing. Also, when the tubes were stored at RT for 1 week and reweighed, there was less change in weight (indicating less evaporation), with the non-wax seals. The weight data are shown below.

| Type Of Seal | Gm Before Freezing | Gm After Freezing | Gm Lost |
|---|---|---|---|
| Non-Wax | 3.0094 | 2.9944 | 0.0150 |
| Wax | 3.0008 | 2.9650 | 0.0358 |
| Vaseline ® | 3.0082 | 2.9512 | 0.0570 |

These results indicate that the non-wax seal is more resistant to freeze-thaw conditions. Using the non-wax mixture of 1:3 ratio of LDPE+Oil, it was found that the addition of solvent red #27 caused an increase in viscosity. This property has some advantages such as increasing the stability of the non-wax seal.

EXAMPLE IX

A Retractable Non-wax Polymer Seal in PCR Reaction Tubes Containing Taq DNA Polymerase and dNTP's (Exper. MK242, 243) A non-wax sealer material (called PE sealer), was prepared from a mixture of low density polyethylene (LDPE), and heavy mineral oil at a ratio of about 1:4. In a glass beaker, 5.6 gm of LDPE was combined with 22.4 gm of heavy mineral oil and 1.4 gm of heavy mineral oil containing 0.1% solvent red #27 (oil red O). The mixture was heated to about 90–100° C. and mixed until homogeneous. At RT this formed a red colored, soft, gel-like solid mass.

Into each of 80 PCR reaction tubes (0.2 ml polypropylene, Robbins Scientific, Sunnyvale Calif.), was dispensed about 3.5 µl (4.4 mg) of PE sealer that had been heated to about 103° C. in an aluminum pan. The dispenser used was an 8 tipped, multichannel pipettor (Labsystems Oy, Helsinki, Finland).

A PCR reagent mix was prepared at about 4.5× concentration (4.5× PCR mix), so that a 5.5 µl aliquot contained the desired amount of Taq DNA polymerase (Taq), dATP, dCTP, dGTP and dTTP (dNTP's), $MgCl_2$ and 10× PCR buffer (500 mM KCl, 1% Triton® X-100, 100 mM Tris-HCl, pH 9.0 @ 25° C.), to perform PCR when DNA template and primers were added and the final volume was increased to 25 µl of water. The 4.5× PCR mix consisted of aqueous solutions of 0.13 µl of 5 units/µl Taq (Promega Corp., Madison Wis.), 0.2 µl of pooled dNTP's @ 25 mM each (Promega), 1.5 µl of 25 mM $MgCl_2$, 2.5 µl 10× PCR buffer and 1.2 µl of water per 5.5 µl.

A 5.5 µl aliquot of 4.5× PCR mix was dispensed into each reaction tube containing about 4.4 mg of PE sealer. Retractable non-wax seals were then prepared by melting and centrifugation. The sealing procedure was to centrifuge the tubes at about 1500 rpm (about 300 R.C.F.), while heating them with a hot air blower to about 77° C. for about 0.5–1 minute to melt the sealing material, then turn off the heat to quickly cool them below the mp (about RT), to solidify the sealer while still centrifuging. The entire cycle took about 4.5 minutes.

The resulting product (called a ReadyWell™), is a PCR reaction tube containing about 5.5 µl of PCR reagent sealed under a layer that is thinner than is possible using prior art methods. The containers were stored at −20° C. After 3 weeks, the seals were inspected and found complete as indicated by no observable loss of liquid under the layers. They were then tested using PCR for release of the reagent when melted.

The preloaded and PE sealed PCR reagents were tested in the PCR using water containing DNA template and PCR primers. The DNA template to be amplified was pBR322 plasmid DNA from E. coli (Promega). The 16 base oligonucleotide primers were pBR322 EcoR I (clockwise) and pBR322 BamH I (counter-clockwise), (both Promega), which complement the ends of a 393 base pair segment on the pBR322 DNA template.

A PCR "sample mix" was prepared in water without any dNTP's, or Taq. The sample mix contained about 0.004 micrograms of pBR322 DNA, and about 0.04 nanomoles of each primer per 0.020 ml of water. Into each of 6 PE sealed tubes was dispensed 0.020 ml of sample mix so that the final reaction volume will be 0.025 ml when the PE seal is melted.

Previous tests have shown that due to insufficient mass of material, the PE seal is a non-barrier system, which retracts and leaves the aqueous reagent exposed to the atmosphere as soon as it is melted. Since the PCR machine used did not have a heated lid to prevent condensation inside the tubes, a 13 mg parafin wax bead was added to each tube to provide a vapor barrier during the PCR.

For the PCR, the samples were thermocycled for 35 cycles of; 60 seconds @ 94° C., 30 seconds @ 55° C., and 60 seconds @ 72° C.

The PCR products were analyzed by agarose gel electrophoresis (AGE). Agarose (NuSieve™ 3:1, FMC Bioproducts, Rockland Me.), was prepared as a 3% gel in TBE buffer (89 mM Tris, 89 mM borate, 2 mM EDTA, pH 8), containing 0.5 micrograms/ml of ethidium bromide stain. About 60 ml of melted gel solution was cast into a 10 mm deep plastic tray of about 13×8 mm.

The tray had two plastic combs suspended about 1 mm from the bottom to form two parallel rows of sample wells in the gel. With one of the longer edges oriented as the "top" of the gel, one comb was about 5 mm inside of, or "below", the top edge and the other comb was positioned about 3.5 mm below the first. The combs had 28 teeth separated by 2 mm wide spaces, 10 mm long. The teeth themselves were 1.5 mm thick and 2.5 mm wide so that the distance between the center of each tooth was 4.5 mm, which is one half the 9 mm distance between well centers of a standard 96 well microplate. Each comb is positioned so that the teeth project down into the melted gel in the tray and are removed when the gel is cooled and solidified. This leaves a row of sample wells that can be conveniently loaded using standard multichannel pipettors.

The PCR samples were diluted about ⅔ in gel loading solution (17% glycerol, 1.3% Ficoll@, 0.07% SDS, 0.013% bromophenol blue in TBE buffer). About 8 µl of each diluted sample was loaded into corresponding wells in the gel. The AGE was run horizontally for about 1 hour at 100 volts and 50 milliamps, then subilluminated with U.V. light and photographed with Polaroid® #66 5 instant film.

With U.V. illumination, PCR product was visible as fluorescent bands in the gel for all 6 tubes. These results indicate that the PE sealed PCR reagents were released from under the seal during the PCR and were active enough after 3 weeks storage at −20° C. to produce amplified pBR322 DNA.

Using the same preparation method used for polypropylene tubes, 5.5 µl aliquots of $MgCl_2$ solution (0.75 ml 10× buffer, 2.25 ml 25 mM $MgCl_2$, 4.5 ml water and 0.01 ml blue food color #1), were each sealed under about 3.2 mg of PE sealer in a polycarbonate container. The polycarbonate container was a PCR reaction plate with 96 individual wells of 0.2 ml volume (Stratagene Inc., La Jolla Calif.). These seals were found to be complete and free of any leakage as indicated by no observed leaching of the blue color into 30

µl of water overlaid on top of the seals for 24 hours. Also, the seals showed no observable damage after 4 cycles of freezing in dry ice (−70° C.), and thawing at RT.

While the invention has been described with references to certain specific embodiments, it is understood that changes may be made by one skilled in the art and it would not thereby depart from the spirit and scope of the invention which is limited only by the claims appended hereto.

What is claimed is:

1. A method for preparing a retractable seal solidified wax over an aqueous reagent in a reaction container such that said reagent is separated from contact with the atmosphere, and wherein the amount of said solidified wax is not sufficient when melted to a liquid under gravity to separate said reagent from contact with the atmosphere, comprising the steps of:

a. combining said reagent and said wax in said container,
 b. heating said wax until said wax has melted to a liquid,
 c. centrifuging said melted wax so that it is forced by centrifugation to form a liquid wax layer over said reagent that completely separates said reagent from the atmosphere, and;
 d. cooling said liquid wax layer to form a solid wax layer during said centrifugation.

2. The method of claim 1 wherein said reagent is selected from the group consisting of heat resistant enzymes.

3. The method of claim 1 wherein said reagent is selected from the group consisting of enzyme substrates.

4. The method of claim 1 wherein said reagent is selected from the group consisting of nucleic acids.

5. The method of claim 1 wherein said reagent is selected from the group consisting of antibodies.

6. The method of claim 1 wherein said reagent is selected from the group consisting of antigens.

7. The method of claim 1 wherein said reagent is selected from the group consisting of avidins and streptavidins.

8. A method for preparing a retractable seal of solidified grease over an aqueous reagent in a reaction container such that said reagent is separated from contact with the atmosphere, and wherein the amount of said solidified grease is not sufficient when melted to a liquid under gravity to separate said reagent from contact with the atmosphere, comprising the steps of:

a. combining said reagent and said grease in said container,
 b. heating said grease until said grease has melted to a liquid,
 c. centrifuging said melted grease so that it is forced by centrifugation to form a liquid grease layer over said reagent that completely separates said reagent from the atmosphere, and;
 d. cooling said liquid grease layer to form a solid grease layer during said centrifugation.

9. The method of claim 8 wherein said reagent is selected from the group consisting of heat resistant enzymes.

10. The method of claim 8 wherein said reagent is selected from the group consisting of enzyme substrates.

11. The method of claim 8 wherein said reagent is selected from the group consisting of nucleic acids.

12. The method of claim 8 wherein said reagent is selected from the group consisting of antibodies.

13. The method of claim 8 wherein said reagent is selected from the group consisting of antigens.

14. The method of claim 8 wherein said reagent is selected from the group consisting of avidins and streptavidins.

15. A method for preparing a retractable seal of solidified polymer mix over an aqueous reagent in a reaction container such that said reagent is separated from contact with the atmosphere, and wherein the amount of said solidified polymer mix is not sufficient when melted to a liquid under gravity to separate said reagent from contact with the atmosphere, comprising the steps of:

a. combining said reagent and said polymer mix in said container,
 b. heating said polymer mix until said polymer mix has melted to a liquid,
 c. centrifuging said melted polymer mix so that it is forced by centrifugation to form a liquid polymer mix layer over said reagent that completely separates said reagent from the atmosphere, and;
 d. cooling said liquid polymer mix layer to form a solid polymer mix layer during said centrifugation.

16. The method of claim 15 wherein said reagent is selected from the group consisting of heat resistant enzymes.

17. The method of claim 15 wherein said reagent is selected from the group consisting of enzyme substrates.

18. The method of claim 15 wherein said reagent is selected from the group consisting of nucleic acids.

19. The method of claim 15 wherein said reagent is selected from the group consisting of antibodies.

20. The method of claim 15 wherein said reagent is selected from the group consisting of antigens.

* * * * *